(12) United States Patent
Kang et al.

(10) Patent No.: US 6,638,543 B2
(45) Date of Patent: Oct. 28, 2003

(54) USE OF NATURAL EGFR INHIBITORS TO PREVENT SIDE EFFECTS DUE TO RETINOID THERAPY, SOAPS, AND OTHER STIMULI THAT ACTIVATE THE EPIDERMAL GROWTH FACTOR RECEPTOR

(75) Inventors: Sewon Kang, Ann Arbor, MI (US); Gary J. Fisher, Ypsilanti, MI (US); John J. Voorhees, Ann Arbor, MI (US)

(73) Assignee: Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 10/085,978

(22) Filed: Feb. 27, 2002

(65) Prior Publication Data

US 2002/0137693 A1 Sep. 26, 2002

Related U.S. Application Data

(60) Provisional application No. 60/271,894, filed on Feb. 27, 2001.

(51) Int. Cl.[7] .......................... A61K 35/78; A61K 7/42; A61K 6/00; A01N 25/00
(52) U.S. Cl. .................... 424/757; 424/59; 424/401; 514/859
(58) Field of Search .................... 424/757, 59, 401; 514/859

(56) References Cited

U.S. PATENT DOCUMENTS 5,665,367 A * 9/1997 Burger et al.
5,824,702 A 10/1998 Wei
6,207,667 B1 * 3/2001 Matsuno et al.
6,423,747 B1 7/2002 Lanzendorfer

FOREIGN PATENT DOCUMENTS

| EP | 0 100 613 A1 | | 2/1984 |
| JP | DW 1995-027620 | * | 11/1994 |
| KR | 2001 001 290 A | | 1/2001 |
| WO | WO 98/13020 A1 | | 4/1998 |
| WO | WO 9936050 A1 | * | 7/1999 |

OTHER PUBLICATIONS

James Varani. "Heparin–Binding Epidermal–Growth–Factor–Like Growth Factor Activation of Keratinocyte ErbB Receptors Mediates Epidermal Hyperplasla, a Prominent Side–Effect of Retinold Therapy". Journal of Investigative Dermatology, vol. 117, No. 6, 2001, Great Britian.

* cited by examiner

Primary Examiner—Christopher R. Tate
Assistant Examiner—Randall Winston
(74) Attorney, Agent, or Firm—Bradley Ruben

(57) ABSTRACT

Many human conditions, often skin conditions, are treated topically or orally with a retinoid such as retinoic acid or acetretin, which treatment often has the side effect of dry, irritated, and/or peeling skin. The use of soaps, detergents, chemical irritants, and such can also cause these same side effects. These side effects can be reduced or eliminated by the topical administration of an inhibitor, especially a natural inhibitor, of the epidermal growth factor receptor (EGFR), administered concomitantly with the retinoid, separately from the retinoid (such as on an as needed basis), or both. Administration of the two together is facilitated by a composition suitable for topical application and comprising both the retinoid and a natural EGFR inhibitor. Preferred natural inhibitors are genistein and other isoflavones extracted from natural occurring substances, or simple derivatives of such substances.

14 Claims, 1 Drawing Sheet

USE OF NATURAL EGFR INHIBITORS TO PREVENT SIDE EFFECTS DUE TO RETINOID THERAPY, SOAPS, AND OTHER STIMULI THAT ACTIVATE THE EPIDERMAL GROWTH FACTOR RECEPTOR

PRIOR APPLICATIONS

This application is based on prior provisional application serial No. 60/271,894, filed Feb. 27, 2001, the disclosure of which is incorporated herein by reference.

BACKGROUND OF THE INVENTION

1. Field of the Invention

This invention relates to the use of EGF receptor inhibitors, especially those occuring naturally in produce, foodstuffs, and the like, such as the isoflavinoid genistein, for preventing unwanted side effects when retinoids are used topically for treating humans.

2. The State of the Art

Topical retinoid administration has been used to treat a wide variety of dermatological ailments. For example, acne vulgaris has been treated with all-trans retinoic acid (tretinoin), sold under the well-known brand name Retin-A (from Janssen Pharmaceuticals), and the lesser known brand name Avita (from Penederm); oral 13-cis retinoic acid (isotretinoin; sold under the brand name Accutane for oral administration) has been used for severe cases of acne. 9-cis retinoic acid (alitretinoin) has been used topically to treat cutaneous lesions of AIDS-related Kaposi's sarcoma (Panretin brand gel, from Ligand Pharmaceuticals), and systemically to treat chronic eczema and renal cancer. Synthetic retinoids that have been approved for use against acne and psoriasis include adapalene (sold under the brand Differin) and tazarotene (sold under the brand name Tazorac), respectively. Psoriasis also has been treated with the trimethylmethoxyphenyl analogue of retinoic acid ethyl ester (etretinate; sold under the brand names Soriatane (acetretin), and formerly Tegison (etretinate)). Retinoids have also been used for treating other kinds of acne (such as cystic acne and acne rosacea) and various keratinization disorders (such as, ichthyoses (such as lamellar ichthyosis, ichthyosis vulgaris), pityriasis rubra pilaris, and Darier's disease). Retinoids have also been used for skin cancer and chemotheraphy of precancerous lesions and chemoprophylaxis (such as for basal cell and squamous cell carcinomas and keratoacanthoma). Retinoids have also been used for treating such skin conditions as warts, hyperkaratotic eczema of the hands and feet, and cutaneous sarcoidosis. In addition, retinoids have been used for treating photoaged skin, with compositions such as sold under the brand name Renova. Thus, retinoids are widely used both topically and systemically (orally) for a wide variety of conditions.

The present inventors and those working with them have invented other uses for retinoids, including preventing photoaging of human skin (e.g., U.S. Pat. Nos. 5,837,224, 6,130,254, and application No. 615218, filed Jul. 13, 2000), preventing and reversing chronological aging of human skin (e.g., application No. 28,435, filed Feb. 24, 1998), treating post-inflammatory hyperpigmentation in black skin (e.g., U.S. Pat. Nos. 5,750,570 and 6,017,960), preventing UV-induced loss of collagen biosynthesis (e.g., application No. 285,860, filed Apr. 2, 1999), prevention of UV-induced functional vitamin A deficiency (e.g., application No. 418, 413, filed Oct. 14 1999), preventing scarring and inflammation due to acne (e.g., 576,597, filed May 22, 2000). The disclosures of these patents and applications are incorporated herein by reference.

While those trained in the use of retinoids are cognizant of toxicity issues, much more common and predictable are common side effects, such as erythema (redness), scaling, burning, and/or pruritus (itching), especially when retinoids are used long term. E.g., J W Fluhr et al., "Tolerance profile of retinol, retinaldehyde and retinoic acid under maximized and long-term clinical conditions", Dermatology 1999; 199 Suppl 1:57–60.

Protein tyrosine kinases are involved in regulating critical functions in mammalian cells (e.g., cell growth, cell death, inflammation, and so on). There are two classes of protein tyrosine kinases: receptor protein tyrosine kinases and non-receptor protein tyrosine kinases. Many growth factor receptors on cell surfaces have intrinsic protein tyrosine kinase activity (i.e., the receptor protein kinases), so that when the growth factor binds to its receptor on the cell surface, it stimulates the intracellular protein tyrosine kinase activity. This intrinsic activation initiates a signal transduction cascade that typically results in cell growth and survival (e.g., effects expected from growth factors).

EGFR (Epidermal Growth Factor Receptor) is a transmembrane protein that includes a bound protein tyrosine kinase (PTK) in the intracellular or cytoplasmic portion, and hence the EGFR has "intrinsic" protein tyrosine kinase activity. After EGF binds to the extracellular portion of the EGFR, the intracellular portion having the PTK moiety can be activated by phosphorylation with ATP (adenosine triphosphate), releasing ADP in the process. When the PTK enzyme portion of the EGFR is activated, it acts on its substrate, which is another EGFR (if one is nearby). (Depending on the particular receptor, there may be a few receptors or there may be thousands of receptors in a given cell's membrane.) The activated EGFR activates an adjacent EGFR by phosphorylating its cytoplasmic portion (which contains the bound PTK) with the ATP. The phosphorylated EGFR (EGF-R-(P)) with the active PTK enzyme catalyzes various reactions that result in nuclear signalling, up-regulating or down-regulating various genes, with concommitant effects on the cell. While this activation is occurring, the first EGFR bound to the EGF may then bind to another ATP and activate the cytoplasmic portion of yet another EGFR, increasing the nuclear signalling. Thus, as EGFRs are activated, they can activate other EGFRs so that the entire signal is amplified.

In one mode of action, it is known that retinoids cause an elevation in the heparin-binding epidermal growth factor (HB-EGF; one member of the EGF family that binds the EGFR), which, through the nuclear signalling just discussed, causes hyperplasia and subsequent scaling and peeling of the skin, a side effect common to many who use retinoids topically. (E.g., J-H Xiao et al., "Identification of heparin-binding EGF-like growth factor as a target in intercellular regulation of epidermal basal cell growth by suprabasal retinoic acid receptors", The EMBO J., Vol. 18, No. 6, pp. 1539–1548 (1999).) When a pharmacological retinoid is applied topically to skin or taken orally, the EGFR (epidermal growth factor receptor) is activated by the release of HB-EGF. The EGFRs are located on cells in the epidermis, and their activation causes the cells in the lower epidermis to proliferate excessively. The excessively proliferating cells cause upward pressure on the outward migrating cells, resulting in an excessive number of cells arriving at the surface of the skin. This hyperproliferation is manifest as peeling, scaling, and/or dryness of the skin. Retinoids have other modes of action, but this mode is believed to be responsible for many of the side effects that deter patients from continued use of retinoid therapy or decrease the benefit they receive (subjectively trading the discomfort of one problem for a lesser problem). Other than terminating therapy, topically applied emollients, moisturizers, humectants, and the like are the typical adjuncts to topical retinoid therapy for mitigating these detrimental side effects. In human skin organ culture it was shown that synthetic EGFR tyrosine kinase inhibitors blocked actions of HB-EGF induced by micromolar concentrations of retinoic acid. (S. W. Stoll and J. T. Elder, "Retinoid regulation of heparin-binding EGF-like growth factor gene expression in human keratinocytes and skin", Exp. Dermatol., 1998: 7:391–397.) More particularly, it was shown that after exposure to a retinoid, the HB-EGF increased, but the EGFR tyrosine kinase inhibitors prevented this increase from causing hyperplasia.

The medical arts have been focussing on the EGFR in connection with anti-cancer therapies because links have been shown between the EGFR subfamily of tyrosine kinases and human cancers, including that various tumors express EGFR. Thus, researchers have been looking towards tyrosine kinase inhibitors as anticancer agents because of the existence of EGFR expression by tumor cells. F. Ciardiello, "Epidermal Growth Factor Receptor Tyrosine Kinase Inhibitors as Anticancer Agents", *Drugs* 2000, 60 Suppl. 1, 25–32; and E. Raymond et al., "Epidermal Growth Factor Receptor Tyrosine Kinase as a Target for Anticancer Therapy", id. at 15–23 (the disclosures of which are incorporated herein by reference). These inhibitory compounds include an extremely wide variety of molecules, including monoclonal antibodies, immunotoxin conjugates, ligand-toxin recombinant proteins, EGFR protein tyrosine kinase inhibitors, and tyrosine kinase inhibitor-ligand conjugates. As the identified cancers that express EGFR include lung, colorectal, advanced gastric, pancreatic, ovarian, breast, and prostate, administration of these compounds is by injection (system or direct acting) or orally. Additionally, more advanced synthetic compounds are more selective and more potent than more naturally occuring compounds. The nuclear signalling mediated by EGFRs can be decreased by inhibiting the binding of EGF to the receptor, by inhibiting the binding of the EGF-EGFR complex to ATP, and/or by inhibiting the activation of the EGFR substrate by (EGF-R-Ⓟ).

Certain inhibitors of protein tyrosine kinase at lower concentrations inhibit other tyrosine kinases at higher concentrations. Among these are EGF-R inhibitors including AG-494 (a member of the tyrphostin family of tyrosine kinase inhibitors), AG-825 (5-[(Benzthiazol-2-yl) thiomethyl]-4-hydroxy-3-methoxybenzylidenecyanoacetamide), AG-1478 (4-(3-Chloroanilino)-6,7-dimethoxyquinazoline) and 4-aniloquinazoline derivatives (W. A. Denny, "The 4-anilinoquinazoline class of inhibitors of the erbB family of receptor tyrosine kinases," *Farmaco* 2001 January–February;56(1–2):51–6, discussing both reversibly and irreversibly binding analogs), EI-146 (an Erbstatin analog), methyl-2,5-dihydroxycinnamate, HDBA (2-Hydroxy-5-(2,5-dihydroxybenzylamino)-2-hydroxybenzoic acid; Onoda et al., *J. Natural Products*, 52:1252, 1989), Lavendustin A, RG-13022 (a non-phenolic tyrphostin analog which inhibits the EGFR), RG-14620 (a non-phenolic tyrphostin analog which is selective for the EGFR and long acting), Tyrphostin 23 (RG-50810), Tyrphostin 25 ([(3,4,5-trihydroxyphenyl)-methylene]-propanedinitrile, Gazit et al., *J. Med. Chem.*, 32:2344, 1989; also known as RG-50875), Tyrphostin 46, Tyrphostin 47 (also known as RG-50864 and AG-213), Tyrphostin 51, and Tyrphostin 1.

A review article by S. B. Noonberg and C. C. Benz ("Tyrosine Kinase inhibitors Targeted to the Epidermal Growth Factor Receptor Subfamily—Role as Anticancer Agents", *Drugs,* 2000 Apr:59(4) (the disclosure of which is incorporated herein by reference)) describes various approaches for inhibiting the kinase activity of EGF receptors, including antibodies, immunotoxin conjugates, ligand-binding cytotoxic agents, and small molecule kinase inhibitors.

Small nucleotide inhibitors have also been developed for inhibiting EGFR, as well as for such kinases as JNK, MEKK, and others that activate EGFR signalling. Exemplary U.S. Pat. Nos. include 5,914,269 and 6,187,585 for EGFR inhibition, 5,877,309, 6,133,246, and 6,221,850 for JNK inhibition, 6,168,950 for MEKK inhibition, and other such as 6,054,440, 6,159,697, and 6,262,241 (the disicosures of which are all incorporated herein by reference). Most are disclosed as suitable for transdermal administration to affect the local dermis, via reference to textbook methods for preparing topically-applied compositions, although no reason is given for such treatment (i.e., no dermal condition is identified that might be treated by such therapy), nor is any efficacy shown for transdermal delivery (i.e., there is no evidence that small nucleotide inhibitors can be applied

SUMMARY AND OBJECTS OF THE INVENTION

In light of the foregoing, it would be beneficial to prevent the peeling, scaling, and dryness that accompanies topical and systemic (oral) retinoid therapy without significantly diminishing the desired therapeutic effect, whether by antagonism, competition, or otherwise. It would also be useful to provide this benefit without interfering with or complicating the retinoid treatment regimen, thereby maintaining if not improving patient compliance with the retinoid therapy.

Towards this end, we have discovered that adminstration of one or more compounds that inhibit EGFR signalling reduces the peeling, scaling, and dryness side effects of therapeutically-administered retinoids. Preferably, these compounds include naturally occuring products, such as isoflavones, one example of which is genistein (which is found in raw soy products), although synthetic analogs thereof are also likely to be useful. The inhibitor may a reversible inhibitor, it may irreversibly bind the receptor, or a combination thereof may be used. Preferably, the admistration of the EGFR inhibitor is topically.

Accordingly, this invention provides a method for diminishing the side effects of topical and systemic retinoid therapy through the use of application of an EGFR inhibitor, preferably a natural product, and preferably by topical administration. The administration can be concurrent with the retinoid therapy, such as administering a composition comprising both a retinoid and a natural EGFR inhibitor, it can be administered as desired by the patient, such as with a separate composition comprising a natural EGFR inhibitor and applied as needed by the patient, or it can be a combination of these methods.

In addition, in another embodiment this invention alleviates the symptom of peeling due to hyperproliferation, regardless of the source of the proliferation (which can range from retinoid therapy to sunburn).

In other embodiments, this invention provides various compositions suitable for topical and systemic application to human skin, including a composition comprising a retinoid and an EGFR inhibitor, preferably a composition comprising a combination of a retinoid and a natural EGFR inhibitor, as well as a topical composition comprising an EGFR inhibitor and an emollient, moisturizer, and/or humectant.

In yet another embodiment, this invention provides a cleanser composition, and a composition for ameliorating irritation due to soaps and other compositions causing contact dermatitis characterized by hyperproliferation. More specifically, in one aspect this invention provides a cleanser, comprising a soap or surfactant and an EGFR inhibitor, more preferably an isoflavinoid such as genistein, or a ground or powdered botanical, such as soybeans which contain genistein. In another aspect, the invention provides a dispersion and/or suspension of an EGFR inhibitor, more preferably an isoflavinoid such as genistein, or a ground or powdered botanical, such as soybeans which contain genistein, in a form such as a lotion or cream, for treating contact dermatitis characterized by hyperproliferation.

DETAILED DESCRIPTION OF SPECIFIC EMBODIMENTS

Figure 1:
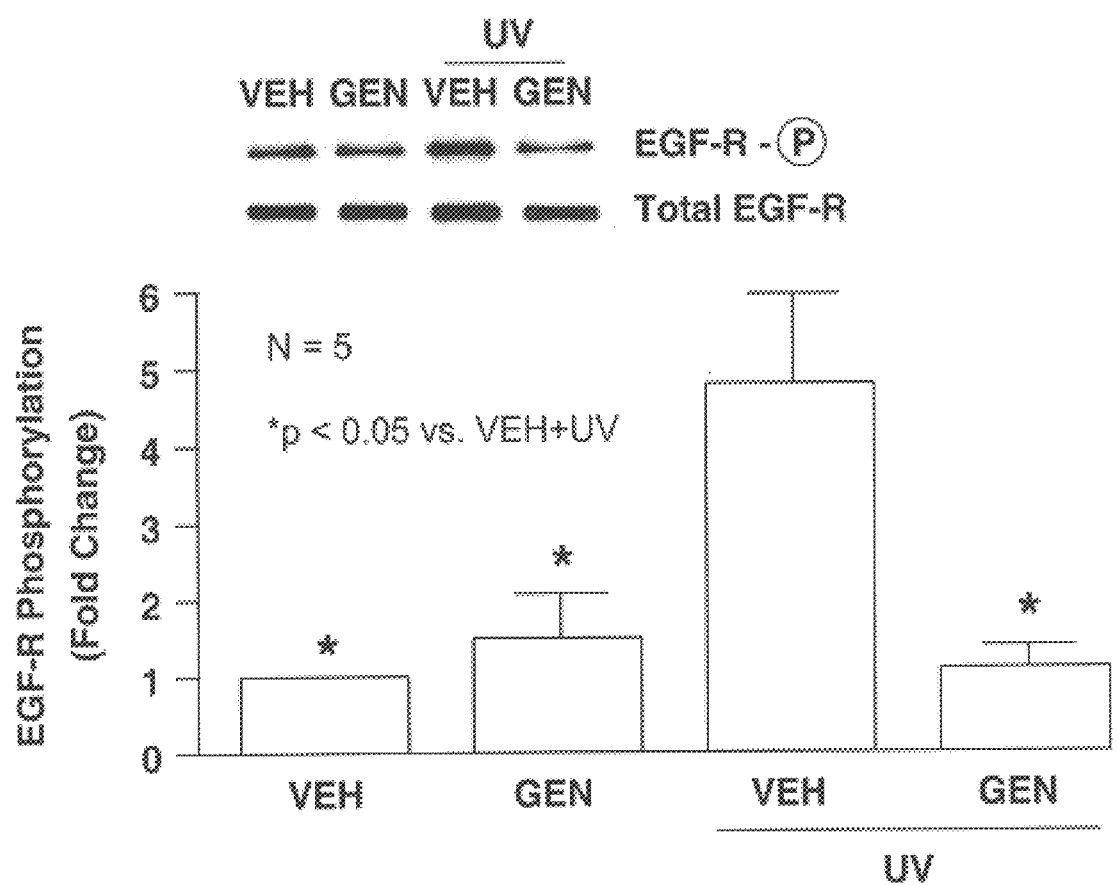
FIG. 1 depicts the ability of genistein to inhibit the activation (phosphorylation) of EGFR by UV radiation of human skin, depicted as the fold change in the amount of phosphorylated receptor, with an insert showing a Western blot comparing the total EGFR with that which has been activated/phosphorylated (EGF-R-Ⓟ).

Natural and synthetic retinoid analogs for topical or systemic administration include vitamin A (retinol), vitamin A aldehyde (retinal), vitamin A acid (retinoic acid (RA)), including all-trans (tretinoin), 9-cis (alitretinoin), and 13-cis (isotretinoin) retinoic acids), etretinate (trimethylmethoxyphenyl analogue of retinoic acid ethyl ester), and others as described in EP-A2-0 379367, U.S. Pat. Nos. 4,887,805, and 4,888,342 (the disclosures of which are all incorporated herein by reference). Various synthetic retinoids and compounds having retinoid activity, to the extent that they exhibit retinoid activity in vivo, are described in various patents assigned on their face to Allergan Inc., such as in the following U.S. Pat. Nos. 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos. 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like, the disclosures of all of the foregoing, and literature references, are incorporated herein by reference. There are also numerous experimental retinoids compounds being developed and undergoing further refinement.

Our prior patents and application on photoaging of human skin teach that UV irradiation of human skin induces MMPs, enzymes that degrade collagen. Using the methodologies described therein, we investigated whether UV irradiation of human skin also induces activation of the EGFR, and whether genistein had any effect on this activation. Using human volunteers (each having given informed consent in writing), selected areas of skin (usually from the hip or buttocks) on each subject were treated with a standard vehicle or genistein (5% dissolved in the standard vehicle), occluded for 24 hours, and then two of the sites, one for genistein and one for the vehicle, were irradiated with UV radiation equivalent to 2 MEDs. Each of the sites was biopsied a certain time after irradiation to determine the effect of genistein on the parameter being examined. For determining the effect of genistein (if any) on EGFR activation/phosphorylation, the time between UV exposure and biopsy of both the irradiated and non-irradiated sites was about 30 minutes. Shown in FIG. 1 is an inset of a Western blot depicting the total EGFR protein under the various conditions for a single human volunteer, and the amount of phosphorylated (activated) receptor protein found under each of the various conditions for that person. The graph in FIG. 1 is a quantitative depiction of the results, the quantitation performed using Western blots from five individual volunteers. As shown in the figure, neither the vehicle nor genistein activated/phosphorylated EGFR in the un-irradiated sites. However, the biopsy of the irradiated sites showed that UV radiation does activate EGFR in human skin, and that genistein inhibits this activation. Hence UV radiation can be used as a substitute agonist instead of retinoids to determine in vivo if a given compound applied topically will prevent the activation of the EGFR. Of course, for in vivo testing the compound must be screened not only for human safety, but also, using this protocol, to assure it is not a UV sunscreen, whereby if EGFR activation after UV irradiation is inhibited, it is known that the inhibition was not due to sunscreen effects from the test compound.

Genistein is part of a group of naturally occuring flavones and isoflavones that also includes quercetin, equol, indolecarbazole, staurosporine, lavendustin, daidzein, and erbstatin that are useful in practicing this invention. These compounds are not only relatively small molecules that can penetrate the skin when applied topically, they are also part of a family of molecules that inhibit protein tyrosine kinases. Various small molecule inhibitors of receptor protein tyrosine kinases that may also be useful in this invention are described by D. H. Boschelli, "Small molecule inhibitors of receptor tyrosine kinases", *Drugs of the Future,* 24(5), 515–537 (1999) (the disclosure of which is incorporated herein by reference). Receptor tyrosine kinase inhibitors can be reversibly bound the to receptor or irreversibly bound. D. W. Fry, "Inhibition of the Epidermal Growth Factor Receptor Family of Tyrosine Kinases as an Approach to Cancer Chemotherapy: Progression from Reversible to Irreversible Inhibitors", *Pharmacol. Ther.,* Vol. 82, Nos. 2–3, pp. 207–218 (1999); and D. W. Fry, "Site-directed irreversible inhibitors of the erbB family of receptor tyrosine kinases as novel chemotherapeutic agents for cancer", *AntiCancer Drug Design* (2000), 15, 3–16 (the disclosures of which are incorporated herein by reference). Unlike the desire of those treating cancer, who select irreversible inhibition, both reversible and irreversible inhibitors are useful for practicing the present invention. Thus, many of the inhibitors mentioned above, and in the publications mentioned above, are likely to be useful in practicing this invention. Generally, inhibitor compounds that are likely to pentrate the skin have a molecular weight of less than about 1000 and are non-polar in nature, although present formulation techniques, including the use of penetration enhancing compositions, can bring additional inhibitor compounds into the gambit of being useful for this invention.

Genistein and its β-glucoside conjugate genistin, can be found in soy milk, tofu (bean curd), miso (bean paste), natto (fermented soybeans), and soy sauce. Other natural EGFR activation inhibitors, and derivatives thereof, include staurosporine, aeroplysinin (K. Hinterding et al., "Synthesis and biological evaluation of aeroplysinin analogues: a new class of receptor tyrosine kinase inhibitors," *Bioorg Med Chem* 1998 August; 6(8):1153–62; H. Waldmann et al., "Selective Inhibition of Receptor Tyrosine Kinases by Synthetic Analogues of Aeroplysinin," *Angew. Chem. Int. Ed. Engl.* 1997, 36, No. 13–14, 1541–1542), lavendustin A (M. S. Symth et al., "Non-amine based analogues of lavendustin A as protein-tyrosine kinase inhibitors," *J Med Chem Oct.* 1, 1993; 36(20):3010–4), piceatannol (3,4,3',5'-tetrahydroxy trans stilbene, a plant secondary natural product; N. C. Mishra et al., "Inhibitory effect of piceatannol, a protein tyrosine kinase inhibitor, on asexual maturation of *Plasmodium falciparum*," *Indian J Exp Biol* 1999 Apr; 37(4):418–20; K. Thakkar, "Synthesis and protein-tyrosine kinase inhibitory activity of polyhydroxylated stilbene analogues of piceatannol," *J Med Chem Oct.* 1, 1993; 36(20):2950–5), hymenialdisine (SK&F 108752) and herbimycin (A. M. Badger et al., "Inhibition of interleukin-1-induced proteoglycan degradation and nitric oxide production in bovine articular cartilage/chondrocyte cultures by the natural product, hymenialdisine," *J Pharmacol Exp Ther* 1999 August; 290(2):587–93), kaempferol and quercetin (and the kaempferol glycosides kaempferol-O3alpharhamnopyranoside and kaempferol-O3-alpha-arabinopyranoside, M. Abou-Shoer et al., "Flavonoids from Koelreuteria henryi and other sources as protein-tyrosine kinase inhibitors," *J Nat Prod* 1993 June; 56(6):967–9; M. Cushman et al., "Synthesis and protein-tyrosine kinase inhibitory activities of flavonoid analogues," *J Med Chem* 1991 February; 34(2):798–806), and erbstatin and tyrphostins (e.g., M. Treuner et al., "Limited selectivity of a synthetic erbstatin derivative for tyrosine kinase and cell growth inhibition," *Biochem Int* 1992 March; 26(4):617–25); a reduced novel benzofluoranthene, tentatively named as (6bS,7R,8S)-7-methoxy-4,8,9-trihydroxy-1,6b,7,8-tetrahydro-2H-benzo[j] fluoranthen-3-one (XR774), from Cladosporium cf. cladosporioides (R. Sadeghi et al., "Differential regulation of CD3- and CD28-induced IL-2 and IFN-gamma production by a novel tyrosine kinase inhibitor XR774 from Cladosporium cf. cladosporioides," *Int Immunopharmacol* 2001 January; 1(1):33–48).

As used in the claims, a "natural" inhibitor of EGFR means a compound, mixture, isolate, extract, or the like having the ability to inhibit the activation of EGFR (e.g., as described below), and which is derived from a substance or organism existing in nature, used as a food source (or nutritional supplement) in its existing form or derived therefrom, or used as a cosmetic or derived therefrom, and minor chemical modifications of such substances. Soy beans, for example, are natural substances, and bean curd is a food source derived therefrom; from either the bean or the curd once can isolate or extract genistein and other isoflavones. Minor chemical modifications to such isolates or extracts are meant those which are relatively simple in nature and analogous to those modifications presently used for foods and nutritional supplements, for some pharmaceuticals, and for foods. Such modifications include, for example, making simple pro-drugs, such as esterification of retinol (usually providing retinyl acetate or retinyl palmitate which convert to retinoic acid in the skin); similar modification include making salts or esters of ascorbic acid, or making different salts of zinc (e.g., zinc sulfate or zinc gluconate to deliver zinc orally), or hydrogenation of vegetable oils, and so on. This is not to ascribe or limit the present invention to any particular mechanism of inhibition, as any given substance that has EGFR inhibitory effects may inhibit the binding of HB-EGF to the EGFR, the binding of EGF-EGFR to ATP, and/or the ability of phosphorylated-EGFR to bind to the substrate (such as an adjacent EGFR).

One screening method for determining the ability of a given compound to inhibit the activation of EGFR is to use cultured cells or an organ culture, preferably using human cells (such as the human skin organ culture used in the above-referenced Stoll and Elder paper) that have been challenged with an agonist known to induce EGFR activation, such as retinoic acid (or another retinoid). The ability of a compound to exhibit retinoid activity can be determined by examining the induction of cytoplasmic retininoic acid binding protein (CRABP) or its DNA (as in U.S. Pat. Nos. 5,871,909 and 5,654,137, the disclosures of which are both incorporated herein by reference) after challenge with the test retinoid compound. Although not essential, but desirable, the test agonist compound can also be used in combination with a Western blot to assure that the total amount of EGFR is unchanged and that only the amount of EGFR activated/phosphorylated is increased (as was the case with the experiments shown in FIG. 1). The cultured cells or organ culture are exposed to the desired agonist compound, then the test inhibitor compound is added, and finally the cells are examined (such via Western blot) to determine the extent of EGFR activation.

An EGFR activation inhibitor compatible with a retinoid used therapeutically for the treatment of humans via topical application that can be admixed into the same composition as the retinoid is provided (assuming it is compatible with the other excipients in that composition as well). The amount of inhibitor used depends on the selectivity of the inhibitor for the EGFR, whether it is a reversible or irreversible inhibitor, its ability to penetrate the skin (the composition may include a penetration enhancer), its stability, its metabolism, and the like. In general, 0.1% to 10%, more preferably about 5% by weight of the composition of a reversible inhibitor is used; lesser amounts of an irreversible inhibitor are used. A combination of reversible and irreversible inhibitors can also be used.

As an alternative to, or in addition to, combining the inhibitor with the retinoid, a separate composition comprising the inhibitor, and a dermatologically suitable carrier, can be applied by the patient as needed, and/or concomittantly with the application of the retinoid. It would be preferable if the patient started the inhibitor "therapy" about sometime prior to starting the retinoid therapy, preferably between one hour and 48 hours prior (depending on the inhibitor used and its mode of administration). Preferably, the inhibitor therapy should be continued for some time after the retinoid therapy has ended, preferably at least one day, more preferably for about one week. As different patients can respond differently, a separate composition is also useful even in combination with a primary composition that is a combination of a retinoid and an inhibitor, as the inhibitor in the primary composition may not provide the optimal effect. Further, for a commercial product that is the retinoid/inhibitor combination, it is likely that there would be only a limited number of specific retinoid/inhibitor strengths, and so a separate inhibitor composition would be a desirable adjunct in the not unlikely event that the inhibitor in the retinoid/inhibitor composition is not as effective as desired for some patients. For the separate inhibitor composition, additional beneficial ingredients that do not interfere with the retinoid therapy or the action of the inhibitor can be present, and especially those that would help to alleviate retinoid therapy side effects. Such ingredients can include humectants, moisturizers, emollients, and even mild antibacterials (such as benzalkonium chloride) and mild anesthetics (such as benzocaine), and compatible mixtures thereof. Additional ingredients as conventionally used, including fragrances, colorants, and the like can be present as desired. The primary retinoid/inhibitor composition, the separate inhibitor composition, or both can be provided as a cream, a gel, a lotion, a spray, and in such other forms as are typically formulated in the dermatological and cosmetics industries.

The present invention may allow increased dosing (application) of retinoid in patients requiring increased dosing. Retinoid dosing, depending on the condition being treated, with this invention will typically range between four times daily and once weekly, although more or less frequent retinoid application may be desirable depending on the condition treated and the patient's response. Likewise, application of the inhibitor may range from four or more times daily to once or fewer times each week, again depending on the side effects of the retinoid treatment experienced by the patient.

As described herein, it should be understood that all retinoid therapy, whether via topical or systemic (e.g., oral) administration, induces HB-EGF, which binds to the EGFR, which then activates itself and causes the side effects that the present invention alleviates. While the in vivo data presented herein used UV light rather than a retinoid as the agonist, and thus by-passed the HB-EGF mode of activating the EGFR, it should be apparent to the artisan of ordinary skill that the present invention provides a method and composition for alleviating any side effect caused by EGFR phosphorylation, whether induced by UV irradiation, retinoid therapy for acne, a cancer therapy, and any other mechanism by which the EGFR becomes activated/phosphorylated. Additionally, while treatments in human have been described herein, retinoids and other compounds that activate the EGFR are also used in vetinary therapies, and the present methods and compositions would alleviate EFGR activation-induced side effects in animals.

Other situations in which EGFR is likely activated occur with irritant contact dermatitis (ICD) from soaps, detergents, surfactants, and other cleansing and cleaning compositions. People who work in human or animal health care or in foodstuff preparation must frequently wash their hands to avoid contamination and cross-contamination. People who work with or are exposed to various chemicals, from lubricants and greases, to paints, to lawn and agricultural chemicals, to detergents and cleaning/degreasing agents, to photographic and printing chemicals, are often exposed to such compositions on a daily or ongoing basis. Chronic exposure of a person's skin to such compositions often results in peeling, cracking (eczema craqué), and/or a thickening of the skin. Such symptoms are highly suggestive of activation of the EGFR, resulting in hyperproliferation of skin cells, leading to peeling, cracking, and thickening of the skin. Unlike allergic contact dermatitis (ACD), where a small amount of the compound functions as an allergen, and the dermatitis is mediated by an immune response (so that a minor future exposure can result in a dramatic dermatitis), irritant contact dermatitis is typically mediated by a dose-response relationship (the higher the exposure, the more vigorous the dermatitis reaction). One method for ameliorating these symptoms is to incorporate an EGFR inhibitor into the soap, detergent, surfactant, or other cleansing or cleaning composition used by the person in an amount of between 0.1% and 10%, more preferably between 1% and 7% by weight. Preferred EGFR inhibitors are the natural or botanically derived inhibitors discussed above, especially genistein and quercetin, and especially those that can be stably incorporated into the cleansing composition. The EGFR inhibitor can be used with a soap (or detergent, etc.) that is in bar or solid form, or one that is provided as a liquid or lotion (including shampoo). For example, a health care worker having to wash his hands perhaps ten to 20 times a day and suffering from ICD due to the chronic and intense exposure to soap benefits from a soap having an EGFR inhibitor prophylatically preventing the ICD. Analogously, a landscaper exposed to fertilizers, herbicides, and fungicides, or an auto mechanic exposed to grease and lubricants, and various hydraulic and heat conducting fluids, would benefit from cleaning up using a soap having an EGFR inhibitor. Still further, as animals suffer similar EGFR-induced ICD, an animal shampoo having an EGFR inhibitor would benefit both the animal and the human shampooer. Of course, the other ingredients in the soap or cleanser are preferably not EGFR-activating, if not also hypoallergenic. Such a cleanser preferably would also include moisturizers, emollients, and the like such as lanolin (not lanolin alcohol).

As seen, various substances, such as retinoids, and various other conditions, such as psoriasis or sunburn, can activate the EGFR. Any substance or condition that activates the retinoic acid receptor (RAR, including the alpha, beta, and gamma subtypes), or any substance that is converted into a compound that activates RAR, can trigger EGFR, resulting in hyperproliferation and peeling. For example, a retinyl ester applied topically is converted to a substance that activates RAR in the outer epidermis. In turn, HB-EFG is produced, which goes to the bottom layer of the epidermis and, as described above, activates the EGFR. Thus, inhibitors of the MAPK (MAPKK, MAPKKK), ERK, phosphorylated-JUN, and the like are useful for preventing activation of the EGFR.

Any substance (such as a retinoid) or condition (skin damage) that acts as a stimulus for growth of the skin can hyperproliferation and thereby cause peeling, to the extent that the growth is caused by the activation of the epidermal growth factor. Thus, as explained above, perceived injury to the skin due to detergents can cause the skin to proliferate, resulting in peeling, even though from a layman's point of view there should not be any injury to the skin from merely washing with soap.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A method for diminishing the side effects of reintoid therapy in a patient in need thereof, comprising topically applying to an affected skin area of the pateint a dermatologically suitable composition comprising an effective amount of a natural EGFR inhibitor selected from the group consisting of genistein, genistin, quercetin, equol, staurosporine, aeroplysinin, indocarbazole, lavendustin, piceatannol, kaempferol, daidzein, erbstatin, and tyrphostins, and mixtures thereof and a suitable carrier, wherein the inhibitor is administered to the patient prior to retinoid therapy, during retinoid therapy, and/or after retinoid therapy.

2. The method of claim 1, wherein the retinoid used in the therapy is a natural retinoid.

3. The method of claim 2, wherein the retinoid is a natural retinoid selected from the group consisting of retinoic acid, all-trans retinoic acid, 13-cis retinoic acid, 9-cis retinoid acid, retinol, retinal, retinoic acid esters, and mixtures thereof.

4. The method of claim 1, wherein the retinoid used in the therapy is a synthetic retinoid.

5. The method of claim 4, wherein the retinoid is a synthetic retinoid selected from the group consisting of adapalene, tazarotene, and mixtures thereof.

6. The method of claim 1, wherein the retinoid therapy is for the treatment of a skin condition selected from the group consisting of acne, acne scarring, eczema, keratinization disorders, cancer, precancerous lesions, chemoprophylaxis, warts, sarcoidosis, treating photoaged skin, preventing photoaged skin, treating chronologically aged skin, preventing chronologically aged skin, post inflammatory hyperpigmentation, UV-induced loss of collagen biosynthesis, and combinations thereof.

7. The method of claim 1, wherein the natural EGFR inhibitor is present in the form of a compound, mixture, isolate, or extract that is derived from soy.

8. The method of claim 7, wherein the natural EGFR inhibitor is genistein, genistin, diadzein, or a mixture thereof.

9. The method of claim 8, wherein the EGFR inhibitor is derived from soy beans or soy bean curd.

10. The method of claim 1, wherein said inhibitor is applied at least prior to the retinoid therapy.

11. The method of claim 1, wherein said inhibitor is applied at least during the retinoid therapy.

12. The method of claim 11, wherein said retinoid and said inhibitor are combined in a single composition.

13. The method of claim 11, wherein the retinoid for the retinoid therapy is administered topically.

14. The method of ciaim 11, wherein the retinoid for the retinoid therapy is administered systemically.

\* \* \* \* \*